United States Patent [19]

Comparetto

[11] Patent Number: 4,728,330

[45] Date of Patent: Mar. 1, 1988

[54] PROSTHETIC BONE OR TOOTH IMPLANT AND A METHOD OF SURGICALLY IMPLANTING THE SAME

[76] Inventor: John E. Comparetto, 108 Cropper St., Chincoteague, Va. 23336

[21] Appl. No.: 270,467

[22] Filed: Jun. 4, 1981

Related U.S. Application Data

[63] Continuation of Ser. No. 32,311, Apr. 23, 1979, Pat. No. 4,349,058, and a continuation-in-part of Ser. No. 763,623, Jan. 28, 1977, Pat. No. 4,150,675.

[51] Int. Cl.⁴ .................................................. A61F 2/28
[52] U.S. Cl. ........................................ 623/16; 623/18; 433/177
[58] Field of Search .............................. 623/11, 16–23; 128/92; 433/177, 173, 176, 178

[56] References Cited

U.S. PATENT DOCUMENTS

| | | | |
|---|---|---|---|
| 544,389 | 8/1895 | Seeger | 433/220 |
| 2,258,207 | 10/1941 | Irwin | 433/173 |
| 2,668,531 | 2/1954 | Haboush | 623/18 |
| 2,781,758 | 2/1957 | Chevalier | 623/23 |
| 3,879,767 | 4/1975 | Substad | 623/18 |
| 4,170,990 | 10/1979 | Baumgart et al. | 623/18 |

Primary Examiner—Richard J. Apley
Assistant Examiner—David J. Isabella
Attorney, Agent, or Firm—Shoemaker and Mattare, Ltd.

[57] ABSTRACT

A prosthetic bone or tooth implant device is disclosed which includes a generally U-shaped cap portion (69) with an upper convex surface. The implant used in bone prosthesis after an osteotomy is performed by an elongated osteotome (30) having a blade comprised of at least one curved portion (38) and at least one flange portion (42). The underside of the U-shaped cap conforms identically to the shape of the osteotome blade, so that when the device is implanted its lower surface will lay perfectly flush against the surface of the bone which has been cut. The implant is affixed to the bone by means of a pin (62) connected at one end to the underside of the implant and which is inserted at its other end into the medullary canal (55) within the bone which has been severed. In order to permit the implant to be used even when the osteotomy is angular the pin is connected to the cap of the implant by means of a ball (67) and socket joint, a universal hinge or an integral hinge which utilizes its natural flexibility to swing the cap to a variety of implant positions. The pin is made of compressible material in order that it can be inserted within the canal and expand after insertion to secure the implant to the bone. A plurality of pin structures are disclosed which provide different methods of securing the implant to the osteotomy.

17 Claims, 24 Drawing Figures

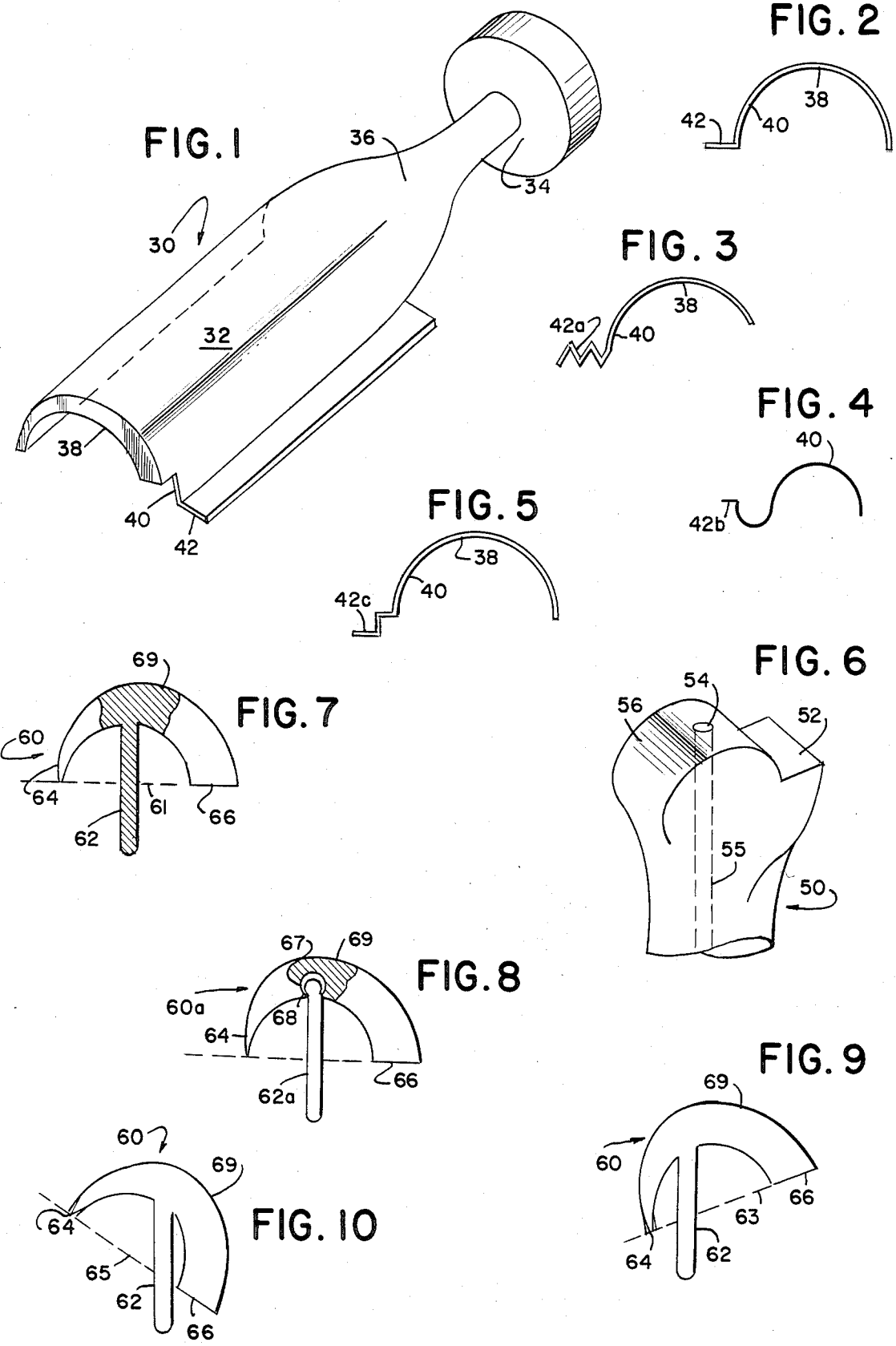

PROSTHETIC BONE OR TOOTH IMPLANT AND A METHOD OF SURGICALLY IMPLANTING THE SAME

BACKGROUND OF THE INVENTION

This application is a continuation of application Ser. No. 032,311, filed Apr. 23, 1979, now U.S. Pat. No. 4,349,058 and a continuation-in-part of Ser. No. 763,623, filed on Jan. 28, 1977 now U.S. Pat. No. 4,150,675, the contents of which are incorporated by reference herein.

The present invention relates generally to surgical implants and more particularly to a new and improved prosthetic bone or tooth implant.

Many bone and tooth deformities lend themselves to correction by means of surgical procedures, which include cutting the bone and implanting an artificial prosthetic device or implant to replace a portion or all of the bone. Most of the conventional bone implants utilize a pin or plug that inserts intramedullarly and relies only upon the pin or plug to retain the implant in a fixed position relative to the bone to which it is attached. These devices are generally used in replacing joints and are not configured to include a plurality of separate surfaces of contact which will act together with a pin to retain the implant on the bone.

Townley, U.S. Pat. No. 2,934,065, discloses a prosthetic implant designed to replace all or part of a femoral head and neck. The implant of Townley includes a head portion 12 and a pin 10 inserted into the medullary canal. Although Townley does include head portions 11 and 18 which bear upon the sides of an osteotomy, the pin 10 and head 12 are rigid, and the bottom of the cap portion is flat, so that this implant can only be used in conjunction with a limited number of surgical procedures. The implant of Townley is neither capable of being adapted to a variety of angulapositions, nor of being placed upon any bone other than one which has been cut along a straight line.

Hodosh, U.S. Pat. No. 3,790,507, comprises a tooth implant with a head portion 10 and a plurality of insert pins 14. These pins are neither designed to be inserted into a medullary canal nor to move so as to enable one pin to provide flexibility for the implant so that it may be used in conjunction with a variety of osteotomies. Further, implant 10 has no structure capable of retaining the implant on a bone to which it is attached, as illustrated by FIGS. 3 and 4 in which the implant 10 merely rests upon the upper surface of the gingiva 28.

The prosthesis of Freeman, et al., U.S. Pat. No. 3,925,824, includes an outer convex surface and a cylindrical inner fixation surface. There are several inherent drawbacks to this prosthesis: the first is that the inner cylindrical surface requires a plurality of circumferential grooves therein to receive and engage the part of the bone upon which it is placed; the second that the rigid configuration of the inner surface limits the number of positions in which the implant can be placed upon a bone which has been cut. Further, this type of prosthetic socket member has retaining means only on its inside surface and does not include a flexible pin to assist in the snug retention of the implant upon a bone.

Similar problems have arisen in conjunction with other prior art implants. In Bentley, et al., U.S. Pat. No. 3,946,445, an implant is disclosed which includes medullary pin 11 or 21. This pin, however, is the only suitable means of affixing the implant to the bone, and does not provide a connection with the top of the bone which would permit the cap to be placed on a variety of angularly situated osteotomies. Charnley, U.S. Pat. No. 3,953,899, comprises a femoral implant which is attached to a bone being operated upon by means of cement, and does not rely in any way upon the structure of the implant to retain the same upon the portion of the bone being cut. The device of Hutter, Jr., et al., U.S. Pat. No. 3,964,106, relies upon cement and a complex threepiece combination device in order to simulate a knee joint.

Timmermans, U.S. Pat. No. 2,679,245, discloses a prosthesis which includes a curved cap portion a or a' and an elongated stem portion i or i'. Rotation of this implant is minimized by the combination of the stem and the two pins h located on opposed sides of the plastic cap. It is further clear that the central shaft or stem of this prosthesis is designed to be rigid, and it is not contemplated that such an implant could be used in conjunction with a plurality of osteotomies that are taken along different angles. Nor is there any disclosure therein that the implant can be used in conjunction with an osteotome which has a cutting blade surface of identical configuration to the lower surface of the implant cap. In fact, it would be virtually impossible to use only one osteotome which would have a configuration identical to the bottom surface of Timmermans' implant, as it is comprised of two U-shaped portions which combine to form an umbrella-like configuration.

It is apparent that none of these prior art implants are capable of solving the same problem that the implant of the current invention solves. None of these devices could be used as implants in conjunction with a plurality of bones that have been cut along different angles, and none of them disclose an implant of simple structure which is capable of being fixedly retained upon the osteotomy. Finally, none of these prior art devices are capable of being used in conjunction with an osteotomy which has been performed by an elongated osteotome of identical configuration as disclosed by the present invention.

OBJECTS OF THE INVENTION

Accordingly, it is a general object of the present invention to provide a new and improved prosthetic bone implant and a method of performing a surgical operation in order to attach the implant to a bone.

Another object of the present invention is to provide a new and improved prosthetic bone implant and a method of implant prosthesis which permits the implant to be used in conjunction with an elongated osteotome of identical configuration, so that the implant can be fit perfectly flush over an osteotomy.

A further object of the present invention is to provide a new and improved prosthetic implant device and a method of implant prosthesis in which the prosthetic implant is retained around a bone by both an implant pin and the structure of an implant head in order that the implant will be fixedly attached to the osteotomy.

An additional object of the present invention is to provide a new and improved prosthetic implant device and a method of implant prosthesis in which the implant is comprised of only a cap portion which can be snapped over the bulbous head structure of an osteotomy.

Yet another object of the present invention is to provide a new and improved prosthetic implant device and a method of prosthesis in which a compressible pin is attached to the implant cap portion so that it will be inserted and expand within a medullary canal of the bone in order to fixedly connect the cap portion to the osteotomy.

A still further object of the present invention is to provide a new and improved prosthetic bone implant and method of implant prosthesis in which the cap portion of the bone implant can be moved in a variety of angles in relation to a compressible pin so that it may be attached to any one of a plurality of angulated osteotomies. Upon further study of the specification and appended claims, further objects and advantages of this invention will become apparent to those skilled in the art.

SUMMARY OF THE INVENTION

Briefly, the above and other objects of the present invention are attained in one aspect thereof by providing a prosthetic bone implant which includes a generally U-shaped flexible cap including both a generally curved surface along its underside and at least one flange portion. The curved surface and flange portion of the cap are identical in configuration to the surface of an elongated osteotome blade which includes at least one curved blade portion and at least one flanged blade portion. This similarity enables the cap to fit snugly and flush over a portion of bone which has been cut by the osteotome blade. The cap further includes a generally curved upper surface and has a flexible pin attached to the lower surface along a concave part of the curved portion thereof, the pin being insertable within the medullary canal of the osteotomy so that the implant may be snugly retained therein. The implant also includes means for angulating the cap with respect to the pin so that the implant can be aligned into a position corresponding to the angle of an osteotomy so that the cap will remain flush upon the upper surface of a bone which has been cut at any angle by said osteotome.

BRIEF DESCRIPTION OF THE DRAWINGS

The above and other objects, features and advantages of the present invention will be more fully appreciated as the same becomes better understood from the following detailed description when considered in connection with the accompanying drawings, in which like reference characters designate like or corresponding parts throughout the several views, and wherein:

FIG. 1 is a perspective view of a cutting tool constructed in accordance with the present invention and showing its cooperative parts;

FIG. 2 is a cross-sectional view of FIG. 1 of the present invention;

FIG. 3 is a cross-sectional view of a second embodiment of a cutting tool of the present invention;

FIG. 4 is a cross-sectional view of a third embodiment of a cutting tool of the present invention;

FIG. 5 is a cross-sectional view of a fourth embodiment of a cutting tool of the present invention;

FIG. 6 is a perspective view of an osteotomy performed using the cutting tool of FIG. 1;

FIG. 7 is a plan view of a prosthetic implant device constructed in accordance with the present invention;

FIG. 8 is a plan view of a prosthetic implant device constructed in accordance with an alternative embodiment of the present invention;

FIG. 9 is a plan view of the prosthetic implant device of FIG. 7 angulated along its abductus axis;

FIG. 10 is a plan view of the prosthetic implant device of FIG. 7 angulated along its adductus axis;

DETAILED DESCRIPTION

Figure 11:
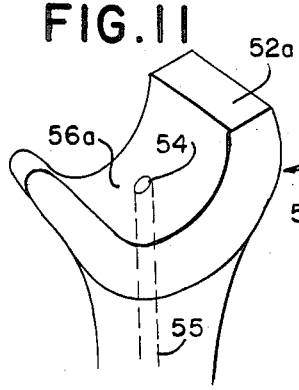
FIG. 11 is a perspective view of a second osteotomy performed using the cutting tool of FIG. 1.

Referring now to the drawings and more particularly to FIG. 1 thereof, the cutting tool of the present invention is generally indicated by reference character 30 and includes a cutting blade portion 32 which is provided upon one end thereof, a head portion 34 which is provided upon the opposite end thereof and an intermediate shaft portion 36 being located between the blade and head portions and serving to integrally connect the same. More particularly, the blade, shaft and head portions of the instrument may either be of unitary construction or may be fabricated individually and fixedly secured together by suitable means. The cutting tool is preferably formed from tempered steel or other metal, but any suitable material which can be formed with a sharpened cutting edge into the shape desired for the cutting tool can be utilized. It should be especially noted here that the blade configuration could be used as a matrix guide for other cutting means such as a saw or laser beam.

As can best be appreciated from FIGS. 1 and 2, blade portion 32 comprises a primary axially elongated arcuate cutting blade portion 38, as viewed in cross section, and an auxiliary arcuate axially recessed cutting blade portion 40, as well as an outwardly extending planar third cutting blade portion 42. Arcuate portions 38 and 40 are defined by loci which form parts of congruent perfect circles; it will be noted that the only difference between such portions resides in the fact that portion 38 extends to the edge of blade portion 32 at one end of the tool, whereas portion 40 is of lesser axial extent. Arcuate portion 40 is axially recessed toward the head end of the instrument, with a resultant step-like configuration formed by the blades 38 and 40 along their edges. Planar cutting blade portion 42 is disposed along the radius of the circular locus defining blade portions 38 and 40, i.e., that is it intersects with a plane tangential to the outer surface of arcuate section 40 and passing through the intersection of sections 40 and 42. The planar cutting blade portion 42 extends outwardly from the periphery of the circle, and its axial extent corresponds to that of arcuate portion 40, so that portions 40 and 42 together define a larger step-like blade portion relative to the primary blade portion 38, for a purpose to be described more fully hereinafter. Both of the cutting surfaces of blade portions 40 and 42 are axially recessed from the cutting edge of portion 38.

Further, while the configuration of the blade portion 42 has been illustrated in FIGS. 1 and 2 as being planar, the same may alternatively have a non-planar configuration, e.g., jagged or corrugated as illustrated blade portion 42a in FIG. 3, sinusoidal or french curve type as illustrated by blade portion 42b in FIG. 4, or step-like as illustrated by blade portion 42c in FIG. 5. These blade configurations result in increased bone or tooth severance areas created by an osteotomy performed using the cutting tool and desired sections severed in various shapes and sizes.

The cutting tool of FIG. 1 can be used to perform an osteotomy such as that illustrated in FIG. 6 by the osteotomy 50. The upper surface of this osteotomy includes a flat ledge section 52 and a convex section 56 which correspond identically to the configuration of the blade portions of the cutting tool 30 which has severed the bone. Along the upper portion of the convex section 56 is an entrance 54 to the medullary canal 55. As explained more fully hereinafter, this canal will be used to help anchor a prosthetic bone implant upon the osteotomy.

In FIG. 7 a first embodiment of a prosthetic bone implant 60 includes a flexible cap 69 having a flat implant ledge section 66, an arc section 64 and a flexible intramedullary pin 62 which is connected to the underside of the implant by means of an integral hinge. The upper surface of the implant is arcuate and of convex configuration. The underside of the implant 60 includes both a generally concave curved surface and a flat ledge section 66 and is identical in cross-sectional configuration to both upper surface of the osteotomy 50 and the cutting tool 30 which has performed the same. This enables the cap to lie flush upon the osteotomy and the implant device to be positioned snugly over the portion of the bone or tooth which has been severed. Axis 61 is taken normal to intramedullary pin 62 so that the tip of arc section 64 and the flat ledge section 66 will both lie in the same plane upon the axis.

Prosthetic implant 60a illustrated in FIG. 8 is identical to the implant 60 of FIG. 7 except that intramedullary pin 62a has a ball head 67 at one end which is inserted within a socket 68 located on the concave underside surface of the implant. Such an arrangement is merely alternative to the integral hinge section of the implant 60 and demonstrates how the implant can be formed of two pieces rather than only one element. Further, a universal joint or other conventional means of hinging could be used in order that the prosthetic bone implant can be angulated as more fully explained hereinafter.

FIGS. 9 and 10 illustrate the positions of the prosthetic bone implant of FIG. 7 when it is angulated with respect to the normal axis 61. In FIG. 9 the implant 60 is angulated along abductus axis 63 so that ledge section 66 is located above axis 61 and arc section 64 is positioned below axis 61. The implant 60 is angulated in FIG. 10 along the adductus axis 65 so that ledge section 66 is below axis 61 and arc section 64 is above axis 61. These angulations enable implant 60, as well as implant 60a and all of the other hinged implants constructed in accordance with the present invention to be positioned upon an osteotomy which has been performed at any angle by a cutting tool with an identical cross-sectional configuration. The angulation is made possible by the flexible hinge structure of implants constructed in accordance with the present invention, overcomes the problem of conventional implants which could only be used when an osteotomy is taken along an axis perpendicular to the intramedullary canal as illustrated in FIG. 6. This, in turn, greatly limits the number of implants which are necessary for prosthesis.

Figure 12:
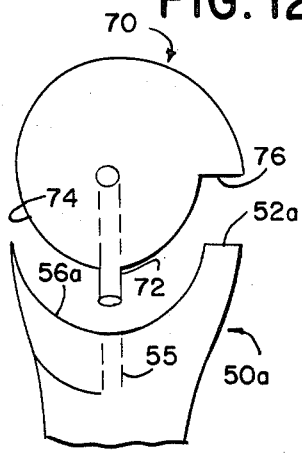
FIG. 12 is a plan view of the osteotomy of FIG. 11 and of prosthetic bone implant to be positioned upon the osteotomy.
Figure 13:
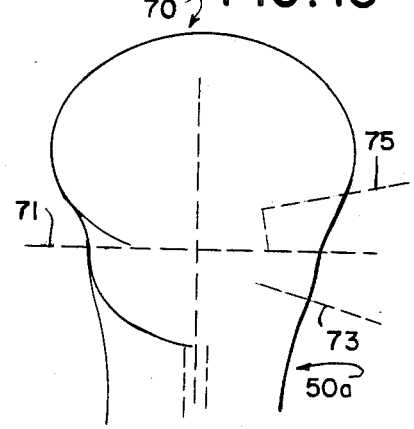
FIG. 13 is a plan view of the osteotomy and bone implant of FIG. 12 after the bone implant has been positioned upon the osteotomy and shows the axes along which the bone implant could be angulated.

FIG. 11 illustrates an osteotomy which has been performed utilizing the cutting tool of FIG. 1 when it is held in a position which is the mirror image of the position in which it is held when it performs the osteotomy of FIG. 6. This osteotomy 50a includes a flat ledge section 52a and a concave section 56a which correspond identically to the configuration of the blade portions of cutting tool 30 which has severed the bone. Along the upper portion of concave section 56a is an entrance 54 to medullary canal 55. It is clear that the implant of FIG. 7 could not be adapted for use with the osteotomy 50a, as it has a concave lower curved surface along its underside. Consequently, a prosthetic implant 70 is provided which has a convex surface 74 located along its underside, a flat ledge section 76 and an intramedullary pin 72. The upper surface of the implant is arcuate and of convex configuration or a configuration that conforms to the general anatomy of the diseased bone or malpositioned bone it is replacing; or the anatomy of a biomechanically sound articular surface to comply with the bone it will articulate with. As illustrated in FIG. 12, this implant 70 is designed to be flushly positioned and snugly fit over the osteotomy 50a. The intramedullary pin 72 is flexibly connected to the implant 70 by an integral hinge or ball and socket, universal joint or other means so that the implant may be angulated with respect to an axis 71 taken normal to the pin. As illustrated in FIG. 13, the implant 70 may be angulated along an adductus axis 73 or an abductus axis 75, in order that the implant may be used whenever an osteotomy is performed at any angle by cutting tool 30.

Figure 14:
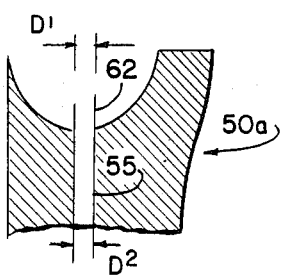
FIG. 14 is a cross-sectional view of the osteotomy of FIG. 11 showing the insertion of an intramedullary pin within the osteotomy.

The intramedullary pin 62 is best illustrated as being inserted within medullary canal 55 by FIG. 14. The pin 62 is perferably comprised of nitinol and it must have a diameter $D_1$ which is equal to or greater than the diameter $D_2$ of the medullary canal 55. The pin may include surgical grade rubber, nylon, or other biologically inert substance coated thereon. The pin is compressible to enable easy insertion into the canal and snug retention within the canal thereafter due to expansion after insertion. The pin would have a memory capability in order to return to its original size and would be able to snugly fill canals of various shapes.

Figure 15:
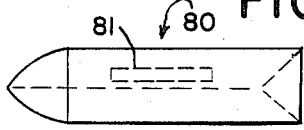
FIG. 15 is a perspective view of a second embodiment of an intramedullary pin constructed in accordance with the present invention.
Figure 16:
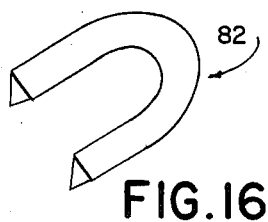
FIG. 16 is a plan view of the third embodiment of an intramedullary pin of the present invention.
Figure 17:
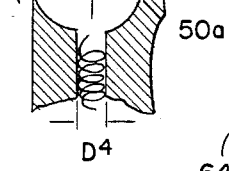
FIG. 17 is a cross-sectional view of the osteotomy of FIG. 11 including a fourth embodiment of an intramedullary pin in accordance with the present invention.

The intramedullary pin can have various configurations as long as it is capable of being fit snugly within the canal, i.e., a compressible prismatic pin 80 which includes nitinol core 81 as illustrated by FIG. 15, a U-shaped looped intramedullary pin 82 as illustrated by FIG. 16 and a coiled nitinol pin 84 as illustrated by FIG. 17. Pin 84 has a diameter $D^3$ when it is elongated as a straight pin before insertion into the canal and has a coil diameter equal to diameter $D^4$ of the medullary canal when it returns to its normal coiled configuration after such insertion.

Figure 19:
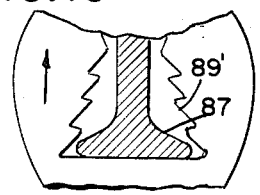
FIG. 19 is a cross-sectional view of another embodiment of a plunger stem constructed in accordance with the present invention.

Alternatively, an implant could be fit snugly within a medullary canal by means of a plunger stem 86 positioned at the bottom of an implant pin and a ratchet clip 89 situated within generally U-shaped surgical grade rubber plug 88. The surgical grade rubber plug 88 is inserted within the canal and the plunger base 86 of pin stem 85 is pushed downwardly within clip 89 so that the outside surfaces of the surgical grade rubber are pushed into abutment with the walls of canal 55 so that the clip will be snugly retained within the canal. In order to best expand the clip against the surgical grade rubber and thusly against the walls of 55, the clip should be angulated or bent inwardly so that the plunger stem 86 forces the clip outwardly. Ratchet clip 89 has a break in the apical region of the clip to allow for the expansion of the clip against the surgical grade rubber; the break in the clip would not be necessary if a larger rounded section would be incorporated into the clip configuration below the deepest ratchet groove. FIG. 19 illustrates a plunger with an inverted cone shaped base 87 which can be used in conjunction with a ratchet clip 89' having more sharply defined ratchet teeth. Alternatively, the base of the plunger can be made of any shape which will act in conjunction with a similarly shaped ratchet clip in order to spread the outer surface of surgical grade rubber material into abutment with the canal walls.

Figure 18:
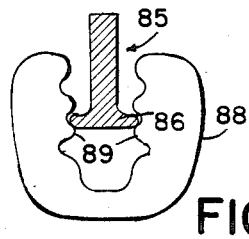
FIG. 18 is a cross-sectional view of a combination plunger and ratchet clip constructed in accordance with the present invention.
Figure 20:
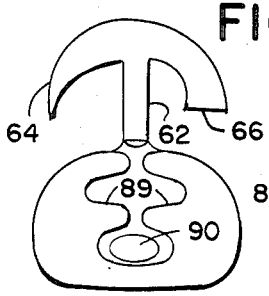
FIG. 20 is a perspective view of the prosthetic bone implant of FIG. 7 in combination with a pellet and ratchet clip.

All of the prosthetic bone implants could be easily adapted for use within a root canal of a tooth as well as within an intramedullary canal of a bone and the implant and clip arrangement of FIG. 20 is particularly applicable to both uses. Surgical grade rubber plug 88 is the same as used in FIG. 18, and a metal ball or pellet 90 is placed within the plug along its lowest inner surface. By using the ball 90 the plug 88 can be maneuvered within a bone or tooth by means of an electromagnet which will move the plug to a desired position within a root or medullary canal. The plug can also be manually placed to the desired depth. Once the plug is positioned, the electromagnet is positioned directly above the plug to pull the ball upwardly between the individual ratchets on clip 89 so as to spread the plug into abutment with the canal walls. Intramedullary pin 62 is connected to ratchet clip 89 and appropriately secured so as to be snugly fit over the bone or tooth.

Figure 21:
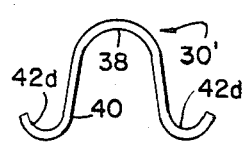
FIG. 21 is a cross-sectional view of a double flanged cutting tool constructed in accordance with the present invention.

Another configuration for the cutting tool is illustrated by tool 30' in FIG. 21, in which two recessed arcuate outwardly extending blade portions 42d are located on opposed sides of arcuate blade portion 38. These portions 42d are flared upwardly and serve to assist in the retention of any wedges which are severed after an osteotomy is performed. The resultant double-flanged osteotomy 50b is illustrated by FIG. 22, and includes two opposed upwardly flanged sections 53 located on opposite sides of bulbous area 57.

Figure 22:
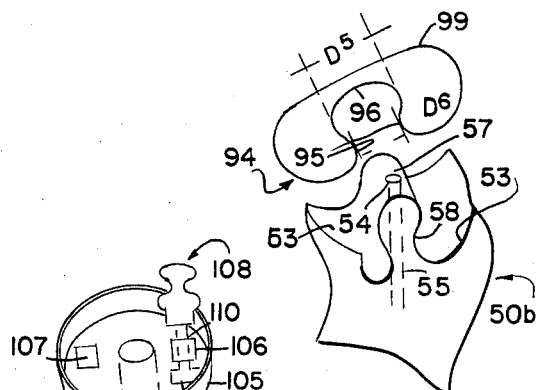
FIG. 22 is a perspective view of an osteotomy performed using the cutting tool of FIG. 21 and a prosthetic implant device to be positioned over said osteotomy.

A double-flanged curved prosthetic implant cap 94 illustrated in FIG. 22 is designed for use in conjunction with osteotomy 50b. The implant has a cross-sectional configuration identical to the blade surface of osteotome 30'. The flanged implant cap has cap portion 99 with an open and a closed end and two downwardly and inwardly directed curved flanged sections 95 along its concave lower surface which are separated by a distance $D^6$. This distance is smaller than the width of bulbous area 57 of the osteotomy, so that the two flanges 95 must be spread apart in order to fit over the bulbous area 57. Accordingly, implant 94 provides a snap fit once the flanges 95 are positioned downwardly around neck section 58 of osteotomy 50b. The implant 94 is further Provided with a wide receiving area 96 located upwardly from said flanged Portions at the closed end of the generally U-shaped implant 94. The width $D^5$ of receiving area 96 is larger than the distance $D^6$, so that the prosthetic implant 94 will be snugly retained upon the osteotomy 50b. Surgical grade rubber would have the necessary resilience for snapping over bulbous area 57.

Figure 23:
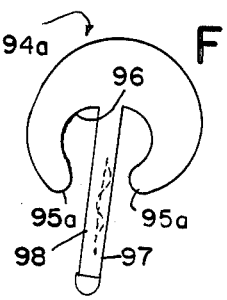
FIG. 23 is a plan view of a second prosthetic bone implant which can be positioned over the osteotomy of FIG. 22.

As illustrated in FIG. 23, a double flanged curved implant 94a can be employed which is provided with inwardly flared curved flanges 95a similar to curved flange sections 95 and with a surgical grade rubber pin stem 97 which can be inserted into medullary canal 55 depending from receiving area 96. The stem 97 further includes coiled nitinol 98 imbedded therein which will provide for better retention of the snap fit cap over the bulbous portion.

Figure 24:
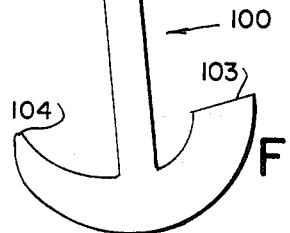
FIG. 24 is a perspective view of yet another prosthetic bone implant and intramedullary pin combination.

A prosthetic implant 100 having a stem 102, a flat ledge portion 103, an arcuate flanged portion 104 and a circular bottom plate 105 at one end of stem 102 is illustrated in FIG. 24 for use in conjunction with clip 108. The bottom plate 105 has a large slot 106 and a narrow slot 107 into which the head portion 112 of clip 108 can be inserted. Clip 108 includes a thin neck portion 110 and a wide head portion 112 which secures the clip 108 to the plate 105, with the remainder of the clip being inserted within a medullary canal to fixedly secure the prosthetic implant 100 upon an osteotomy. In use, an osteotomy will be performed by any of the osteotomes of the present invention so that an arcuate bone surface and a flanged bone surface will remain. Then an implant with a configuration identical to the osteotome is selected to be placed over the bone. The implant cap is angulated to conform to the angle of the osteotomy and the pin is inserted into the canal. Finally, the cap is adjusted so that it will lay flush upon the bone surfaces.

From the foregoing description, one skilled in the art can easily ascertain the essential characteristics of this invention, and without departing from the spirit and scope thereof, can make various changes and modifications of the invention to adopt it to various usages and conditions.

I claim:

1. A physiologically acceptable prosthetic implant for repairing bones or teeth which comprises:

(a) a generally semi-cylindrical U-shaped flexible cap, said cap including a lower generally curved surface along the underside thereof and at least one flange portion, so that said cap will fit snugly over a portion of bone or tooth which has been complimentary shaped, said cap further including a generally curved upper surface;
  (b) a flexible pin attached to said curved surface along the underside of said cap, said pin including means for snugly retaining said implant;
  (c) means for angulating said cap with respect to said pin so that said prosthesis can be aligned into a position so that the cap will lie flush upon the upper surface of a bone which has been complimentary shaped;
  (d) said angualtion means comprising a ball and socket connection between said pin and said cap; and
  (e) said pin being formed of nitinol and having a diameter at least equal to a diameter of a medullary canal into which it will be inserted so that when said pin is inserted into said canal it will fit snugly therein and assist in the retention of said cap.

2. A prosthetic implant according to claim 1 wherein said generally curved lower surface is generally cocave and said flange is a flat ledge portion adapted to lie flush upon a corresponding flat portion said bore, said upper surface being of a generally complementary convex configuration.

3. A prosthetic implant device according to claim 1 wherein said generally curved lower surface is generally convex and said flange is a flat ledge portion adapted to lie flush upon a corresponding flat ledge section said bore, said upper surface being generally convex in a direction opposite from said lower surface and conforming to the appropriate bone anatomy or tooth anatomy.

4. A physilogiocally acceptable prosthetic implant for repairing bones or teeth which comprises:
  (a) a generally semi-cylindrical U-shaped fleixible cap, said cap including a lower generally curved surface along the underside thereof and at least one flange portion, so that said cap will fit snugly over a portion of bone or tooth which has been complimentary shaped, said further including a generally curved upper surface;
  (b) a flexible pin attached to said curved surface along the underside of said cap, said pin including means for snugly retaining said implant;
  (c) means for angulating said cap with respect to said pin so that said prosthesis can be aligned into a position so that the cap will lie flush upon the upper surface of a bone which has been complimentary shaped;
  (d) said angulation means comprising an integral flexible connection between said pin and said cap; and
  (e) said pin being formed of nitinol and having a diameter at least equal to a diameter of a medullary canal into which it will be inserted so that when said pin is inserted into said canal it will fit snugly therein and assist in the retention of said cap.

5. A prosthetic implant device according to claim 4 wherein said pin is formed as a coil, wherein said coil is deformed upon implantation into said mediullary canal and tends to return to its original non-deformed state within said medullary canal to assist in the retention of said cap.

6. A prosthetic implant device according to claim 4 wherein said pin is covered by a compressible material.

7. A prosthetic implant according to claim 6 wherein said compressible material is surgical grade rubber.

8. A prosthetic implant according to claim 4 in which said pin is in the form of a U-shaped loop.

9. A prosthetic implant according to claim 1 wherein said cap has a thin portion and a thick portion, said thick portion being situated at the flange portion of said cap, said thin portion being situated at an edge opposite said flange portion, said upper surface and lower surface of said cap taper from said thick portion to said thin portion along said upper surface and lower surface so as to provide a continuity of thickness to said cap.

10. A prosthetic implant according to claim 1 further comprising a circular bottom plate having upper and lower surfaces and a central hole into which said pin of said cap is retained, a large and narrow slot into which a clip is inserted, each said clip having a thin neck portion extending through said slot, and said clip having a wide head portion abutting the upper surface of said circular bottom plate so as to prevent said clips from moving out of said slot, whereby said plate is inserted within a canal so as to retain said pin and said cap to the bone surface.

11. A prosthetic implant according to claim 1, wherein said cap is a double-flanged curved cap, each flange section being downwardly and inwardly directed along the inner generally curved surface of the cap, wherein the distance between each inner surface of each said flange is less than the width of an area of an osteotomy so that each flange must be spread apart in order to fit over the area to provide a snap fit between the cap and area of said osteotomy.

12. A prosthetic implant according to claim 11 wherein said angulation means is a socket formed in said lower curve surface and said ball is formed at end of said pin.

13. A physiologically acceptable prosthetic implant for repairing bones or teeth which comprises:
  (a) a generally U-shaped flexible cap, said cap including a lower generally curved surface along the underside thereof and at least one flange portion, so that said cap will fit snugly over a portion of bone or tooth which has been compleimentary shaped, said cap further including a generally curved upper surface;
  (b) A flexible pin attached to said curved surface along the underside of said cap;
  (c) means for angulating said cap with respect to said pin so that said prosthesis can be aligned into a position so that the cap will lie flush upon the upper surface of a bone which has been complimentary shaped,
  (d) a plunger means having an enlarged flattened beaded surface attached to the bottom of said pin,
  (e) a generally U-shaped plug which can be inserted within a medullary canal,
  (f) a ratchet clip, situated within said plug, said plunger means being pushed into said plug and retained within said plug by said ratchet clip, said plunger means within said ratchet clip expanding said ratchet clip to push the outside walls of said plug into abutment with the walls of said canal so that said plug, said ratchet clip and said thereby said pin and said cap are snugly retained to the surface of a bone which has been cut complimentary shaped.

14. A prosthetic implant according to claim 13 wherein said ratchet clip is angulated or bent inwardly so as to increase the expansion when siad plunger means is inserted within said plug.

15. A prosthetic implant according to claim 13 wherein said ratchet clip has an apical region and said clip defining a break in said apical region to allow said clip to expand against said plug.

16. A prosthetic implant according to claim 13, wherein said ratchet clip has a large rounded section below the deepest ratchet groove to hold said plunger stem.

17. A prosthetic implant according to claim 13 wherein said plug is made of a surgical grade rubber material.

* * * * *